United States Patent
Nurminen et al.

(10) Patent No.: US 7,038,101 B2
(45) Date of Patent: May 2, 2006

(54) METHOD FOR PRODUCT SEPARATION AND PURIFICATION IN ISO-BUTYLENE DIMERIZATION PROCESS

(75) Inventors: Matti Nurminen, Porvoo (FI); Ronald Birkhoff, Houston, TX (US); Anand Subramanian, Sugarland, TX (US)

(73) Assignee: Neste Oil Oyj, Porvoo (FI)

( * ) Notice: Subject to any disclaimer, the term of this patent is extended or adjusted under 35 U.S.C. 154(b) by 251 days.

(21) Appl. No.: 10/235,321

(22) Filed: Sep. 5, 2002

(65) Prior Publication Data

US 2003/0050522 A1    Mar. 13, 2003

Related U.S. Application Data

(60) Provisional application No. 60/317,272, filed on Sep. 5, 2001.

(51) Int. Cl.
*C07C 2/08* (2006.01)
*C07C 2/14* (2006.01)

(52) U.S. Cl. ............... 585/504; 585/510; 585/809; 585/868

(58) Field of Classification Search ............... 585/504, 585/510, 809, 868
See application file for complete search history.

(56) References Cited

U.S. PATENT DOCUMENTS

| 4,100,220 A | 7/1978 | Bowman et al. ....... 260/683.15 |
| 4,242,530 A | 12/1980 | Smith, Jr. ............... 585/510 |
| 4,375,576 A | 3/1983 | Smith, Jr. ............... 585/510 |
| 4,982,022 A | 1/1991 | Smith, Jr. et al. .......... 568/899 |
| 5,003,124 A | 3/1991 | Smith, Jr. et al. .......... 585/526 |
| 5,231,234 A | 7/1993 | Arganbright et al. ....... 568/697 |
| 5,336,841 A | 8/1994 | Adams ....................... 585/834 |
| 5,345,005 A | 9/1994 | Thankur et al. ............ 568/885 |
| 6,596,913 B1 | 7/2003 | Loescher ................... 585/504 |
| 6,734,333 B1 | 5/2004 | Loescher ................... 585/868 |

FOREIGN PATENT DOCUMENTS

| WO | WO 00/23402 | 4/2000 |
| WO | WO 01/79146 | 10/2001 |
| WO | WO 03/033442 | 4/2003 |

OTHER PUBLICATIONS

PCT International Search Report for International Application No. PCT/FI02/00717 dated Dec. 13, 2002 (3 p.).

*Primary Examiner*—Tam M. Nguyen
(74) *Attorney, Agent, or Firm*—Conley Rose, P.C.

(57) ABSTRACT

A method for operating a dimerization reactor that receives a hydrocarbon feed and produces an output stream comprising a light hydrocarbon component, a dimer and an alcohol component comprises: (a) separating the first output stream into a top stream containing the light hydrocarbon and a bottom stream containing the dimer, with the alcohol being present in the top stream or the bottom stream or both; (b) contacting at least one of the bottom and top streams with a water stream so as to extract at least a major portion of the alcohol therefrom, thereby forming an water/alcohol stream; (c) contacting the water/alcohol stream with a hydrocarbon stream so as to extract at least a major portion of the alcohol present in the water/alcohol stream into the hydrocarbon stream, thereby forming an alcohol-enriched hydrocarbon stream; and (d) feeding the alcohol-enriched hydrocarbon stream into the dimerization reactor.

27 Claims, 6 Drawing Sheets

METHOD FOR PRODUCT SEPARATION AND PURIFICATION IN ISO-BUTYLENE DIMERIZATION PROCESS

RELATED APPLICATIONS

This application claims benefit of U.S. application Ser. No. 60/317,272, filed Sep. 5, 2001, and entitled "Enhancing Reaction Selectivity Control in Isobutylene Dimerization Process Using Recovery and Recycle of C3 Through C6 Alcohol From Iso-Octene Product."

FIELD OF THE INVENTION

The present invention relates to dimerization of isobutylene. In particular, it concerns recovery and recycle of C3 through C6 alcohol from iso-octene product. One purpose of alcohol recycle is to control reaction selectivity in isobutylene dimerization process where acidic catalysts are used (e.g. NExOCTANE process). Preferred embodiments of the invention utilize a tandem liquid extraction process, so as to produce an iso-octene product free of water-soluble oxygenates.

BACKGROUND OF THE INVENTION

A patent application has been published for alternate alcohol recovery methods by distillation, under WO 00/23402 (Fortum Patent), which is incorporated herein by reference. Prior art relates to the use of tertiary butyl alcohol (TBA) for the purpose to control the reaction selectivity. This is described in Petro-Tex Chemical Company U.S. Pat. No. 4,100,220 of Jul. 11, 1978.

As described in WO 00/23402, the addition of water and $C_3$-$C_6$ alcohol is used to control the conversion and the selectivity of the dimerization reactions. $C_3$ through $C_6$ alcohols are formed in the dimerization process through the reaction of water with $C_3$-$C_6$ olefins present in the hydrocarbon feed. The feedstock primarily comprises $C_4$ olefins and paraffins, but may also contain some propylene, and $C_5$-$C_6$ olefins and paraffins.

In the dimerization, an acidic catalyst is used, preferably, ion-exchange resin catalyst. However, as catalysts can be used zeolites and other inorganic catalysts. The ion exchange resin catalyst can comprise sulphonic acid groups and it can be prepared by polymerizing or copolymerizing aromatic vinyl compounds and, thereafter, sulphonating. As examples of aromatic vinyl compounds the following may be mentioned: styrene, vinyl toluene, vinyl naphthalene, vinyl ethyl benzene, methyl styrene, vinyl chlorobenzene, and vinyl xylene. An acidic ion-exchange resin contains typically in average 1.3 . . . 1.9, even up to 2 sulphonic acid groups per one aromatic group. Preferred resins are those based on copolymers of aromatic monovinyl compounds and aromatic polyvinyl, in particular divinyl, compounds, in which the concentration of polyvinylbenzene is approximately 1 . . . 20 wt-% of the copolymer. The particle size of the ion-exchange resin is preferably approximately 0.15 . . . 1 mm.

In addition to the resins already described, also perfluorosulphonic acid resins consisting of copolymers of sulphonylfluorovinyl ethyl and fluorocarbon compounds can be used. Various suitable ion-exchange resins are commercially available, an example of these is Amberlyst 15.

The feedstock for the dimerization contains isobutylene. Depending of the origin of the feedstock the concentration of isobutylene may vary from 10 wt-% to 100 wt-%. Typical feedstock sources are C4 streams from refinery crackers (e.g. FCC, TCC, DCC, RCC), C4 dehydrogenation units (e.g. Catofin, Oleflex) and also isobutylene manufactured from chemicals where isobutylene content may be more than 90 wt-%.

FIG. 1 describes one typical dimerization process with alcohol recovery. The feed (F) is water washed in extraction column 4 and sent to reaction zone (1). The reaction effluent (R1) is distilled in product distillation column (2) for separation of $C_4$ fraction (D1). The bottom product (B1) is directed for further distillation in column 3. The distillate (D2) contains some $C_5$ to $C_8$ hydrocarbons and alcohols formed in the reaction zone and this distillate is routed back into the reaction zone. The bottom product (P1) from column 3 makes the dimerization product.

SUMMARY OF THE INVENTION

According to the present invention, the $C_3$-$C_6$ alcohol that is formed as a by-product in the isobutylene dimerization reaction is recovered from the reaction product and recycled to the reactor inlet. The present invention relates in part to a method for recovery of a mixture of $C_3$-$C_6$ alcohol from the iso-octene dimerization product using liquid extraction with water, and subsequent extraction of the mixed $C_3$-$C_6$ alcohol from the water stream using the net $C_4$ hydrocarbon stream to the isobutylene dimerization reaction section. In this process, the recycle of $C_3$-$C_6$ alcohol to the dimerization section is achieved in two liquid extraction steps.

The alcohol recovery/recycle process disclosed herein preferably utilizes liquid extraction steps. In the conversion of existing MTBE plants to iso-octene production existing equipment can be used to convert to the new service, requiring a minimum of modifications to the existing plant.

BRIEF DESCRIPTION OF THE FIGURES

For a more detailed understanding of the invention, reference is made to the accompanying Figures, wherein.

DETAILED DESCRIPTION OF THE INVENTION

Figure 1:
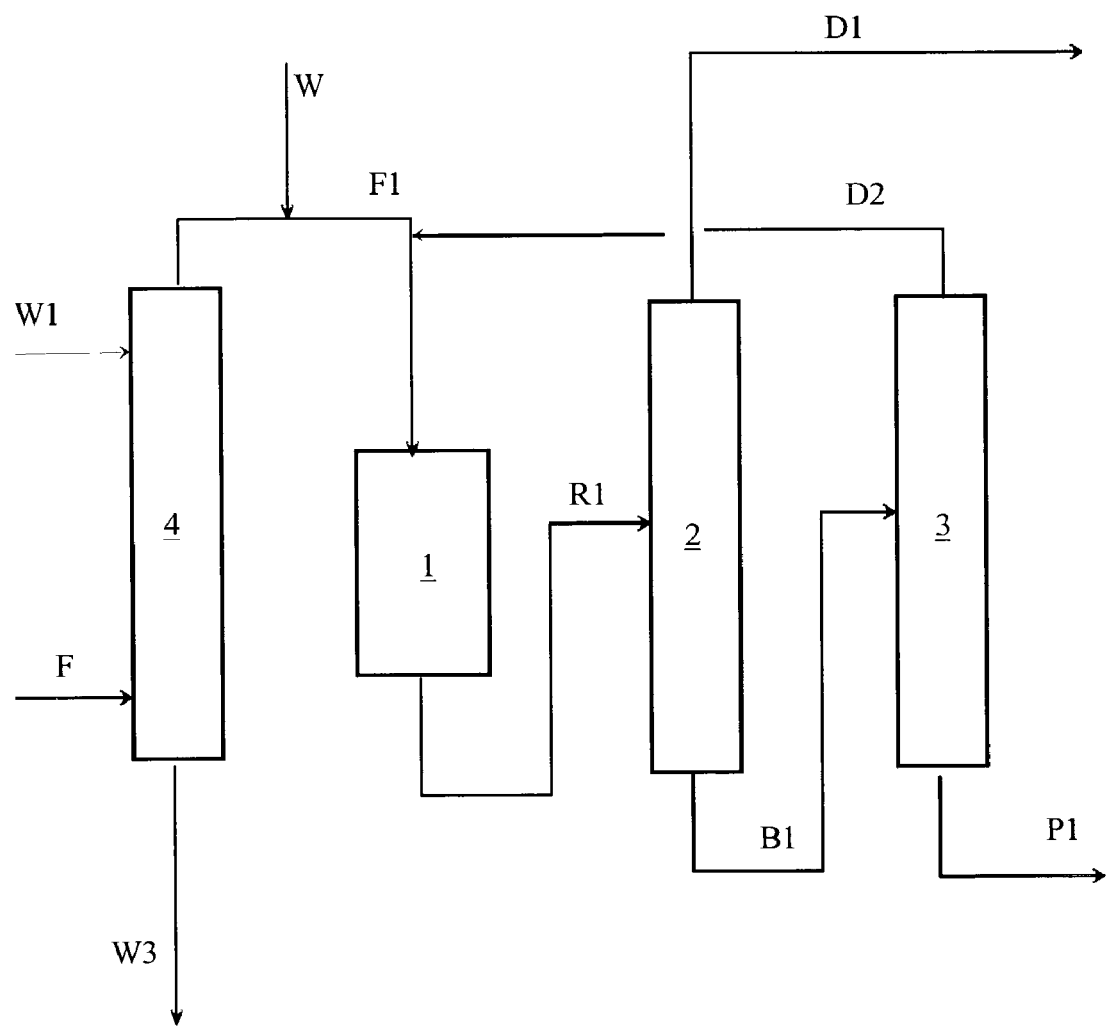
FIG. 1 is a schematic diagram of an isobutylene dimerization process with alcohol recovery (prior art)

For the purpose of producing a high quality gasoline blendstock, isobutylene can be dimerized to form iso-octene, in the liquid phase over an Acidic Ion Exchange resin catalyst, as is known in the art. A by-product of this reaction is the further oligomerization of iso-octene with isobutylene to form larger hydrocarbon components in the series $C_{12}$, $C_{16}$, etc. Hydration of the ion exchange resin catalyst is an effective way to control the selectivity of the overall reaction to iso-octene, thereby minimizing the formation of the larger oligomerization products. For the hydration of the catalyst, $C_4$ alcohols such as tert-butylalcohol (TBA) and sec-butylalcohol (SBA) have been identified as effective components. Other alcohols derived from olefins in the range from $C_3$–$C_6$ components are also effective for the same purpose.

For the purposes of the present invention, the "separation unit" typically designates a distillation system comprising distillation and liquid extraction columns. The columns are preferably connected in series. The feed plate can be selected for each column to be most advantageous in view of the overall process. Likewise, the plates for sidedraw of flows to be recovered or circulated can be selected individually for each column. The distillation and extraction column can be any column suitable for distillation, such as a packed column, or one provided with valve, sieve or bubble-cap trays.

A "reaction section" or "reaction zone" comprises at least one, typically two or three, reactor(s). The reactor can be, e.g., a tubular reactor with multiple pipes, wherein the pipes are filled with catalyst. Other possibilities include a simple tubular reactor, a boiler reactor, a packed bed reactor and a fluidized bed reactor. The reactor used is preferably such in which the catalyst is placed in more than one layer and cooling is introduced between the layers. Preferably at least one of the reactors has a cooling system. For example, the pipes of the tubular reactor with multiple pipes can be cooled. Another example of a suitable reactor is a combination of a fixed bed reactor and a cooler, in which part of the reactor effluent can be circulated back to the reactor via the cooler. The operating pressure of the reactors depends on the type of the reactor and on the composition of the feed, typically it is desired to keep the reaction mixture in liquid phase.

"Isooctene" and "diisobutene" are both products of isobutene dimerization. Thus they can be used interchangeably to designate 2,4,4-trimethyl-1-pentene and 2,4,4-trimethyl-2-pentene or a mixture thereof.

"Reaction mixture" or "reaction effluent" contains the desired product of the dimerization reaction in the reaction zone. When only $C_4$-olefins or only $C_5$-olefins are fed to the process, it is clear that the resulting product of the mutual reactions of the olefins yield dimers. However, when $C_3$-, $C_4$- and $C_5$-olefins are present in the feed, in addition to dimerization, also reactions between $C_4$-olefins and $C_5$-olefins yielding $C_9$-olefins can occur. The word "dimer" is also used for the reaction products in the specification for reasons of simplicity, but it is to be understood that when for example both $C_4$- and $C_5$-olefins are present in the feed, the reaction mixture typically contains also some amount of the $C_9$-olefins and use of the term "dimer" is intended to encompass those.

The feed of the process according to the present invention is a hydrocarbon mixture containing olefins and paraffins. The feed comprises olefins to be dimerized at least 10 wt-%, preferably at least approximately 20 wt-%. As already described, the olefins are selected from the group of linear 1- or 2-butene, isobutene and propylene and linear or branched $C_5$-olefins. Alternatively, the feed can comprise a mixture of any or every of the olefins listed above. Typically, the feed comprises dimerizable components; either $C_4$-olefins, preferably isobutene, whereby iso-octene is produced, or $C_5$-olefins, whereby substituted $C_{10}$-olefins are produced. It is clear that C3-, $C_4$- and $C_5$-olefins can be present in the feed, whereby a great variety of products is produced. The composition of the product flow is discussed later.

According to the first preferred embodiment, in which $C_4$-hydrocarbons are dimerized, the hydrocarbon mixture in the feed comprises at least 10 wt-%, preferably at least approximately 20 wt-% isobutene. The feed can consist of pure isobutene, but in practice, the feedstock readily available comprises $C_4$-based hydrocarbon fractions from oil refining. Preferably, the feed comprises a fraction obtained from isobutane dehydrogenation, when the feed comprises mainly isobutene and isobutane and possibly small amounts of $C_3$- and $C_5$-hydrocarbons. Typically the feed then comprises 40–60 wt-% of isobutene and 60–40 wt-% isobutane, usually there is 5–20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert $C_4$-hydrocarbons and approximately 5 wt-% of $C_3$-, $C_5$- and heavier hydrocarbons altogether.

The feed for producing iso-octene is also possible to select from the group containing $C_4$-fractions of FCC, TCC, DCC and RCC or from the $C_4$-fraction after the removal of butadiene, also called Raffinate 1 of an ethylene unit. Of these FCC, RCC, TCC and Raffinate 1 are preferred, since the hydrocarbon fractions can be used as such, possibly after removing the heavier ($C_{8+}$) fractions. Raffinate 1 is typically composed of approximately 50 wt-% isobutene, approximately 25 wt-% linear butenes and approximately 25 wt-% paraffins. The product from the FCC is typically composed of 10–50, in particular 10–30 wt-% isobutene, 20–70 wt-% 1- and 2-butene and approximately 5–40 wt-% butane. As an example of a typical FCC-mixture, the following can be presented: approximately 30 wt-% isobutene, approximately 17 wt-% 1-butene, approximately 33 wt-% 2-butene and approximately 20 wt-% butane.

Similarly, feed containing more than 90 wt-% of isobutene prepared from chemicals can be used.

According to the second preferred embodiment of the invention, in which $C_5$-olefins are dimerized, the feed comprises olefins selected from the group of linear and branched $C_5$-olefins, or a mixture thereof. Thus, the olefins typically present in the feed comprise linear pentene, 2-methyl-1-butene, 2-methyl-2-butene, 3-methyl-1-butene or 2-ethylpropene. Also some amounts of $C_6$-olefins, typically at least 5 wt-% can be present in the feed.

Typically, the feed in the second preferred embodiment is FCC gasoline, light FCC gasoline, pyrolysis-$C_5$-gasoline, TCC gasoline, RCC gasoline and Coker gasoline, typically the $C_5$-fraction of FCC gasoline, and can thus comprise also some $C_6$-olefins. Advantageously, the FCC fraction is fractionated to obtain as pure $C_5$-olefin fraction as possible where other $C_5$-hydrocarbons are present in less than 15 wt-%, preferably less than 5 wt-%. It is possible to use a fraction comprising also $C_6$-olefins. Typically, the feed then comprises 20 to 60 wt-%, in particular 30 to 50 wt-% $C_5$-olefins, 10 to 30 wt-%, in particular 15 to 25 wt-% $C_6$-olefins and 15 less paraffinic hydrocarbons pentanes.

According to the third preferred embodiment, the feed comprises both $C_4$- and $C_5$-olefins. In this case, the feed is typically selected from the group comprising FCC, TCC, DCC and RCC or from the $C_4$-fraction after the removal of butadiene, also called Raffinate 1 of an ethylene unit, FCC gasoline, light FCC gasoline, pyrolysis-$C_5$-gasoline, TCC gasoline, RCC gasoline and Coker gasoline. A fraction readily available comprises $C_4$ and $C_5$ fractions from FCC. Advantageously, a fraction comprising at least 10 wt-%, preferably at least 15 wt-% $C_4$-olefins and at least 10 wt-%, preferably at least 15 wt-% $C_5$-olefins is used. Typically the amounts of $C_4$-olefins and $C_5$-olefins are approximately equal, although a slight dominance of $C_4$-olefins in the fraction is also usual.

In addition to the hydrocarbon, an oxygen-containing compound (an oxygenate), such as alcohol, is fed into the process in order to slow down the oligomerization reactions of the olefin and to decrease the catalyst poisoning. Instead of alcohol, another possibility is to feed into the process a compound that will form alcohol, like water. The use of oxygenate increases the dimer selectivity whereby the portion of trimers and tetramers of the olefin oligomers decreases. Thus, the fraction of dimers of the formed olefin oligomers is typically at least 80 wt-%. The oxygen containing (and alcohol forming) compound can be fed together with the fresh olefin feed, or it can be fed together with the circulation flow, or directly to the reaction zone.

$C_3$ through $C_6$ range alcohols are formed as a byproduct in the dimerization process through the reaction of water with the associated olefin. For example, isobutylene reacts with water to form tert-butylalcohol (TBA). Water is added to the reaction mixture deliberately to produce such alcohols.

The present invention relates to a novel process for recovering the $C_3$–$C_6$ alcohol from the reaction product, and for recycling the alcohol fraction to the dimerization reactor(s).

In the overall process, an isobutylene-containing stream is fed to the dimerization reaction section. Feedstock can be derived from a typical FCC unit, butane dehydro unit, steam cracker, or other process, and may contain other $C_4$ olefins and paraffins, as well as $C_3$ and $C_{5-6}$ olefins and paraffins. The dimerization reactor effluent is first fed to a distillation tower, in which the unreacted $C_4$ and lighter fraction is removed by fractionation from the heavier reaction products, alcohols, and unreacted $C_{5+}$ fraction. According to the present invention, the crude iso-octene product containing the dimerization product and essentially all of the $C_3$–$C_6$ alcohol is recovered as a bottoms product, and fed to an alcohol recovery step, for the purpose of recycling the alcohol to the dimerization reactor(s).

In the alcohol recovery step, the iso-octene product is contacted with water in a counter-current manner in a liquid-liquid extraction column (3). The water to hydrocarbon ratio employed in this step may vary from 0.1:1 to 100:1 by weight, preferably 0.5:1 to 10:1 by weight, and the operating temperature is preferably between 0 and 200° C., preferably 5 to 150° C., and more preferably about 50° C. In the liquid extraction process almost all, preferably at least 80% by weight, more preferably at least about 90%, and advantageously at least 98%, of the alcohol is removed from the iso-octene product and dissolved in the water phase. The resulting alcohol-containing wash water (W2) is subsequently contacted with the hydrocarbon feed stream (F), and/or with the net hydrocarbon feed stream (D1), either containing mostly $C_4$ hydrocarbons, before being fed into the reaction section in a second counter-current extraction column. The water to hydrocarbon ratio employed in this step may vary from 0.01:1 to 100:1 by weight, preferably 0.1:1 to 4:1 by weight, and the temperature is generally between 0 and 200° C., preferably 5 to 150° C., and more preferably about 45° C. In this second extraction step, almost all, preferably at least 80% by weight, more preferably at least about 90%, and advantageously at least 98% of the alcohol is extracted from the water phase, and dissolved in the hydrocarbon feed stream to the reaction section.

For the liquid extractions a variety of devices such as are well known in the art can be utilized, including single-stage mixed contractors, multi-stage counter-current extraction towers with either trays or packing, multi-stage mechanically agitated liquid-liquid contacting devices, etc.

In a variation of the present process (shown in FIG. 3) the intermediate water/alcohol stream is concentrated by means of distillation. The concentrated alcohol/water stream is then fed to the hydrocarbon feed extraction step for the purpose of alcohol recovery. In order to optimize the efficiency of the extraction processes, each extraction step may utilize multiple water feeds, possibly with different alcohol contents.

Figure 4:
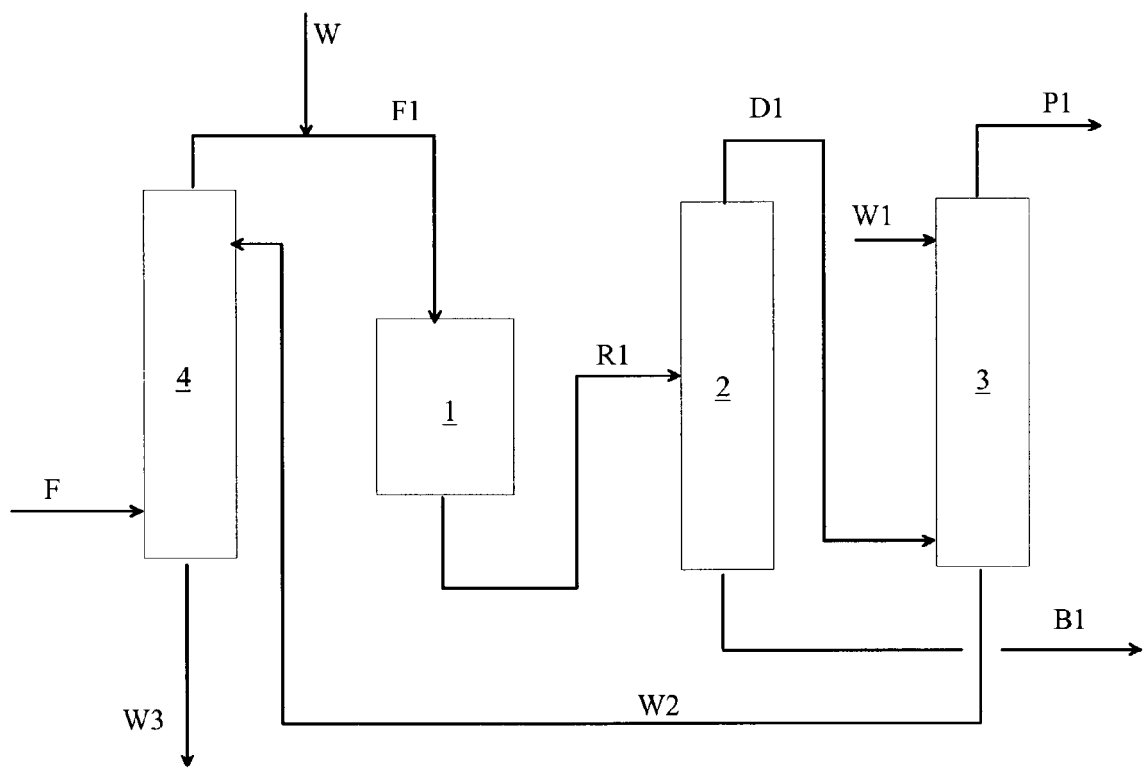
FIG. 4 is a schematic diagram of an isobutylene dimerization constructed in accordance with a second alternative embodiment of the present invention.

In another variation of the process (shown in FIG. 4) the $C_3$–$C_6$ alcohol may be recovered from the unreacted $C_4$ fraction produced in the first distillation tower, either exclusively, or in combination with recovery from the iso-octene product.

Figure 2:
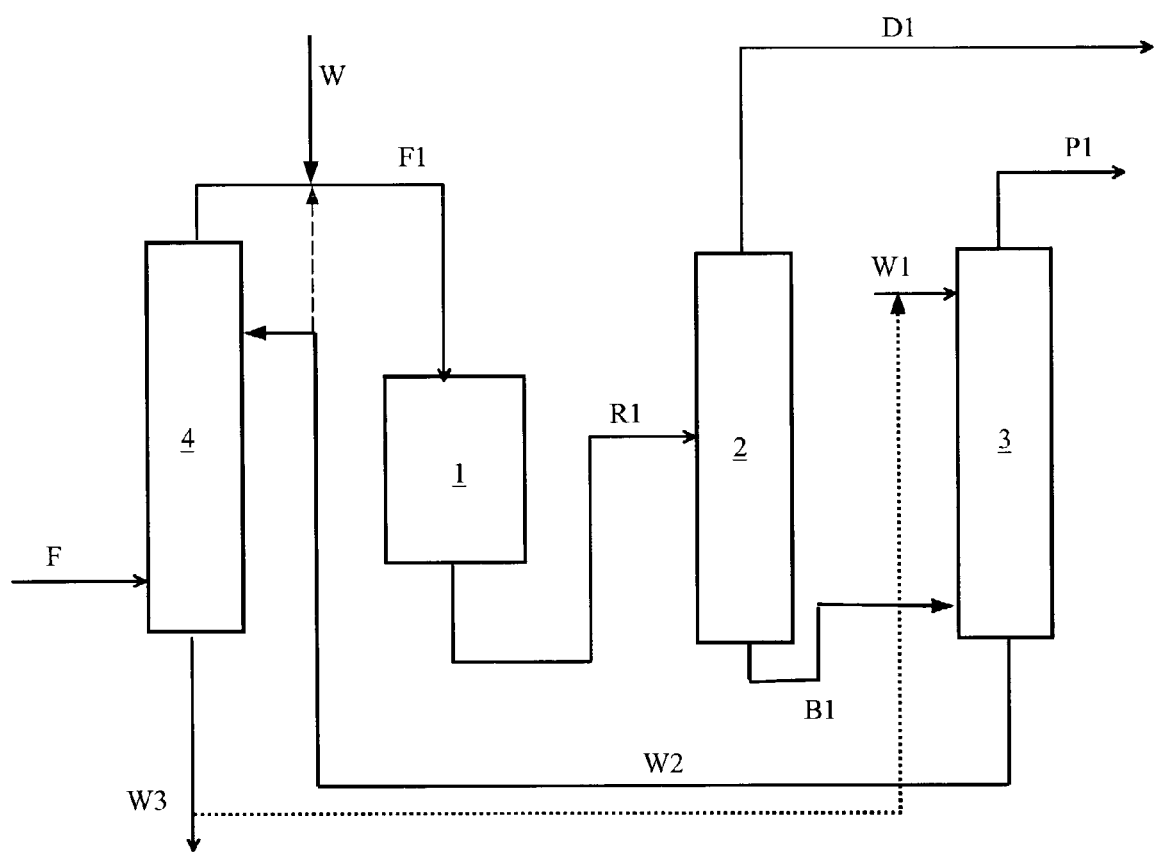
FIG. 2 is a schematic diagram of an isobutylene dimerization constructed in accordance with a preferred embodiment of the present invention.

One embodiment of the novel product separation process is presented in FIG. 2. Hydrocarbon feed containing isobutylene and other $C_3$–$C_6$ olefins and paraffins (F1), also containing oxygenate such as alcohol and water is fed to the reaction zone (1), where the dimerization reaction takes place. The reaction effluent (R1) flows to a product distillation column (2) on a feed plate in the middle part of the column. The operating parameters in the product distillation column are selected such that most of the $C_3$–$C_6$ alcohols are drawn of the bottom with the crude iso-octene product (B1). The product distillation column also produces a $C_4$ fraction at the top (D1), essentially free from oxygenates other than water. The crude iso-octene product (B1) is sent to a product extraction column (3) where it is contacted in a counter-current manner with wash water (W1). Water-soluble $C_3$–$C_6$ alcohols are thereby recovered in the water phase from the crude iso-octene product, along with other water-soluble components. The iso-octene product is recovered from this extraction step as the lighter hydrocarbon phase (P1). Wash water now containing the $C_3$–$C_6$ alcohol (W2) is sent to a feed extraction column (4), where it is contacted in a counter-current manner with the hydrocarbon feed to the dimerization process (F). In this extraction step the $C_3$–$C_6$ alcohol are recovered in the hydrocarbon phase from the water phase. The feed extraction step yields the olefin feed (F1) as the lighter hydrocarbon phase which is sent to the reaction zone (1), and a wash water stream (W3), essentially free of alcohol. A small amount of water (W) may be added to the hydrocarbon feed prior to the dimerization reactor, to facilitate the control of selectivity in the dimerization process.

Figure 3:
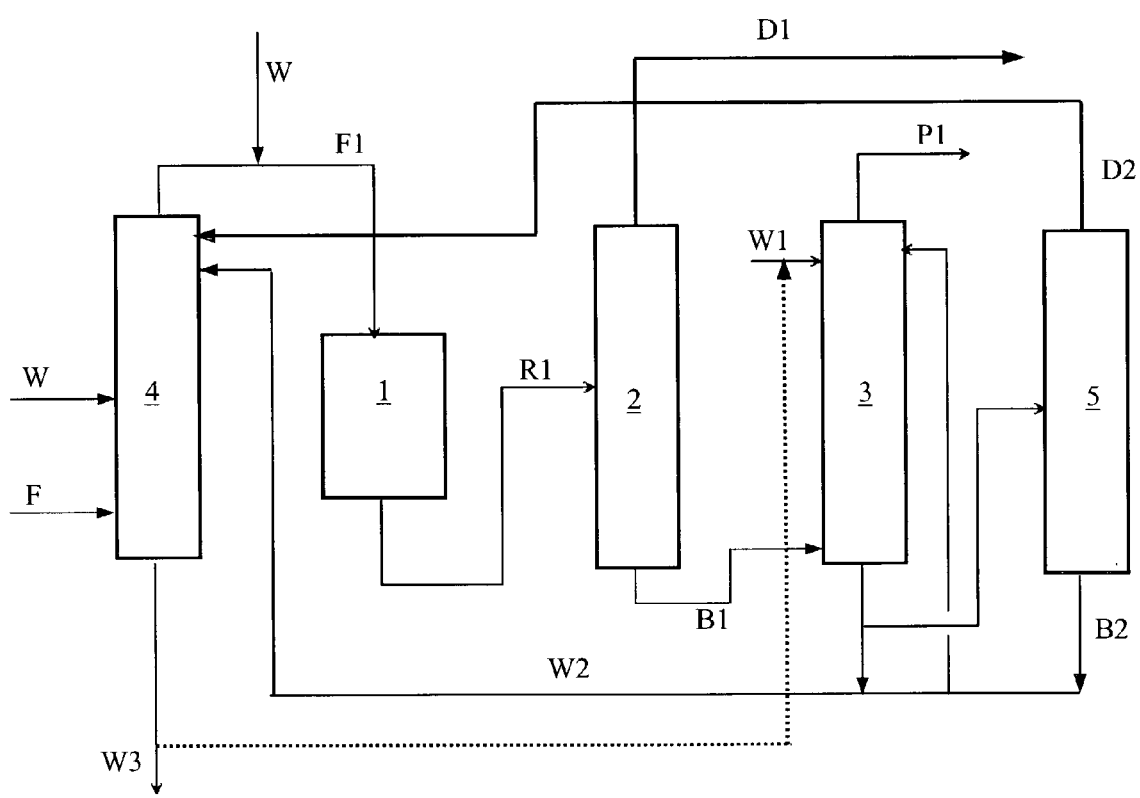
FIG. 3 is a schematic diagram of an isobutylene dimerization constructed in accordance with a first alternative embodiment of the present invention.

A first variation of the product separation process, which is the preferred embodiment of the invention, is presented in FIG. 3. In this process, all or a portion of the alcohol containing wash water (W2) from the product extraction column (3) is sent to an alcohol distillation column (5) where a portion of the wash water feed (W2) is recovered as a concentrated mixture of $C_3$–$C_6$ alcohol and water at the top (D2), and cleaned wash water essentially free of alcohol at the bottom (B2). The remaining portion of W2 can be sent directly to the feed extraction column as practiced in FIG. 2. In this variation all or a portion of the clean wash water (B2) may be recycled to the product extraction column (3) for further extraction of $C_3$–$C_6$ alcohol. Also, all or a portion of B2 may be sent to the feed extraction column (4) directly. The concentrated alcohol water mixture (D2) is sent to the feed extraction column (4) directly. A small portion of D2 may be mixed with the hydrocarbon feed (F1) to the dimerization reaction section to replace all or part of the water flow W. The feed extraction column may have a single wash water feed location or multiple wash water feed locations on different plates or packed sections in the column, for the different wash water sources discussed here. In addition, clean water (W) may be added.

It will be understood that, in any of the embodiments described herein, all or a portion of any of the clean water streams, such as (W3), can be recycled to any of the clean water feeds, such as (W1). An example of this is shown in phantom (dotted lines) in FIGS. 2 and 3. Likewise, all or a portion of any of the alcohol-laden water streams, such as (W2) or (D2), can be injected into the feed stream either instead of or in conjunction with additional water stream (W). An example of this is shown in phantom (dashed lines) in FIG. 2. In addition, optimization of the feed locations and quantity of the wash flows can be conducted by anyone skilled in the art, with the objective to maximize the recovery of alcohol from the wash water. Certain constraints exist in the feed extraction column, wherein a minimum ratio of water to hydrocarbon flow is desired to assure adequate washing to remove water soluble components from the hydrocarbon feed (F) which may cause deactivation of the dimerization catalyst downstream.

In a second variation (FIG. 4) of the product separation the process parameters in the product distillation column (2) are selected such that $C_3$–$C_6$ alcohol are fully recovered in the distillate (D1) from the column. Subsequently, the distillate D1 is washed in a distillate extraction column in a counter current manner with wash water, for the purpose of recovering the $C_3$–$C_6$ alcohol into the wash water stream. The washed C4 fraction is the light hydrocarbon phase in the extraction process and leaves the extraction column essentially free of alcohol. Wash water containing $C_3$–$C_6$ alcohol is then recycled to the feed extraction column or sent to an alcohol distillation column for concentration of the alcohol. Handling of the water and alcohol containing water streams is then similar to the preferred embodiment of the product separation process.

Figure 5:
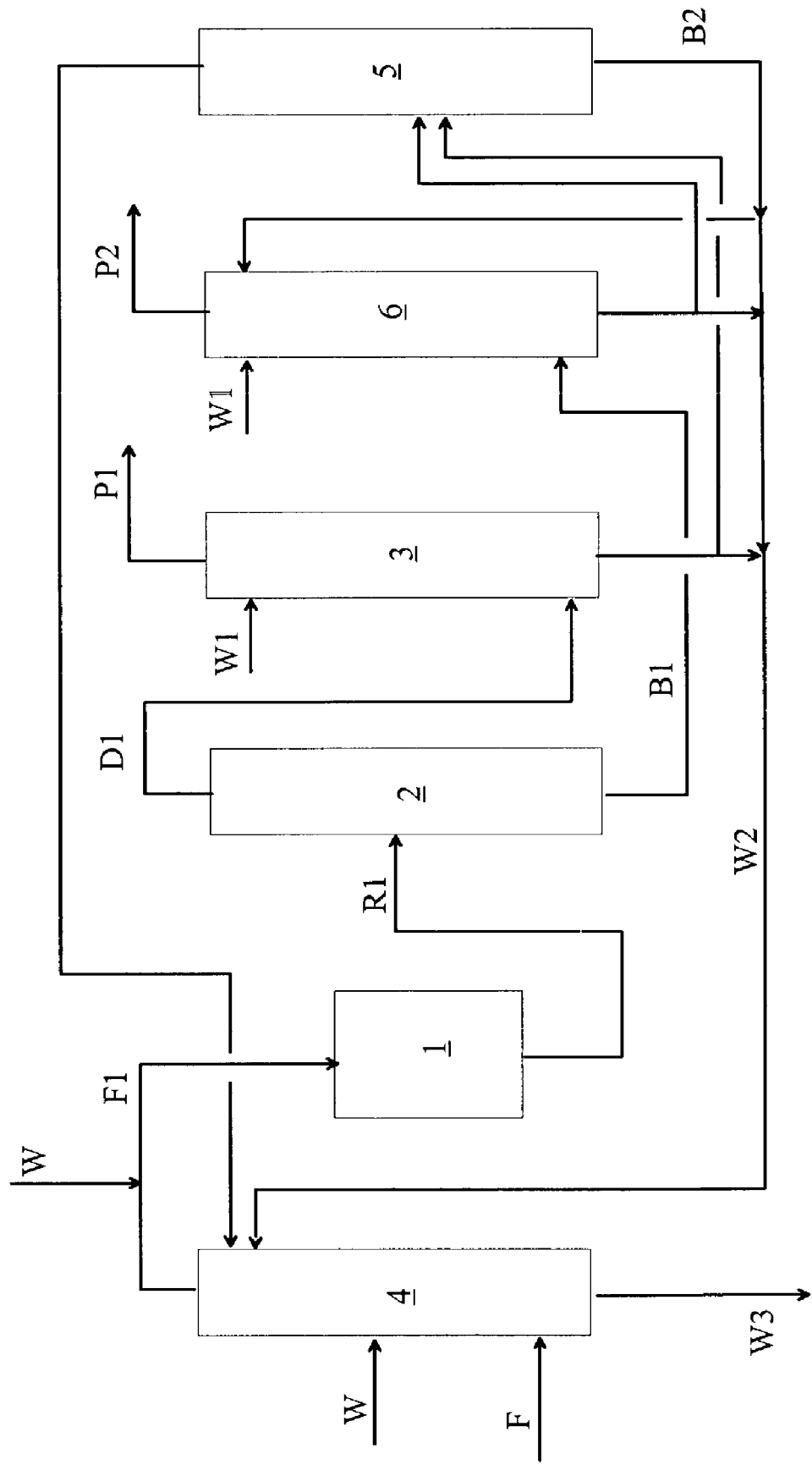
FIG. 5 is a schematic diagram of an isobutylene dimerization constructed in accordance with a third alternative embodiment of the present invention.

In a third variation of the product separation process (FIG. 5) the process parameters in the product distillation column (2) are selected such that $C_3$–$C_6$ alcohol is recovered both from the bottom (B1) as well as the top (D1) of the column. Recovery of the alcohol from these streams is practiced as presented in the first and second variation of the process. Wash water flows from both the product and distillate extraction steps may be combined for recycle to the feed extraction. Handling of the water and alcohol containing water flows is then similar to the preferred embodiment of the product separation process.

Figure 6:
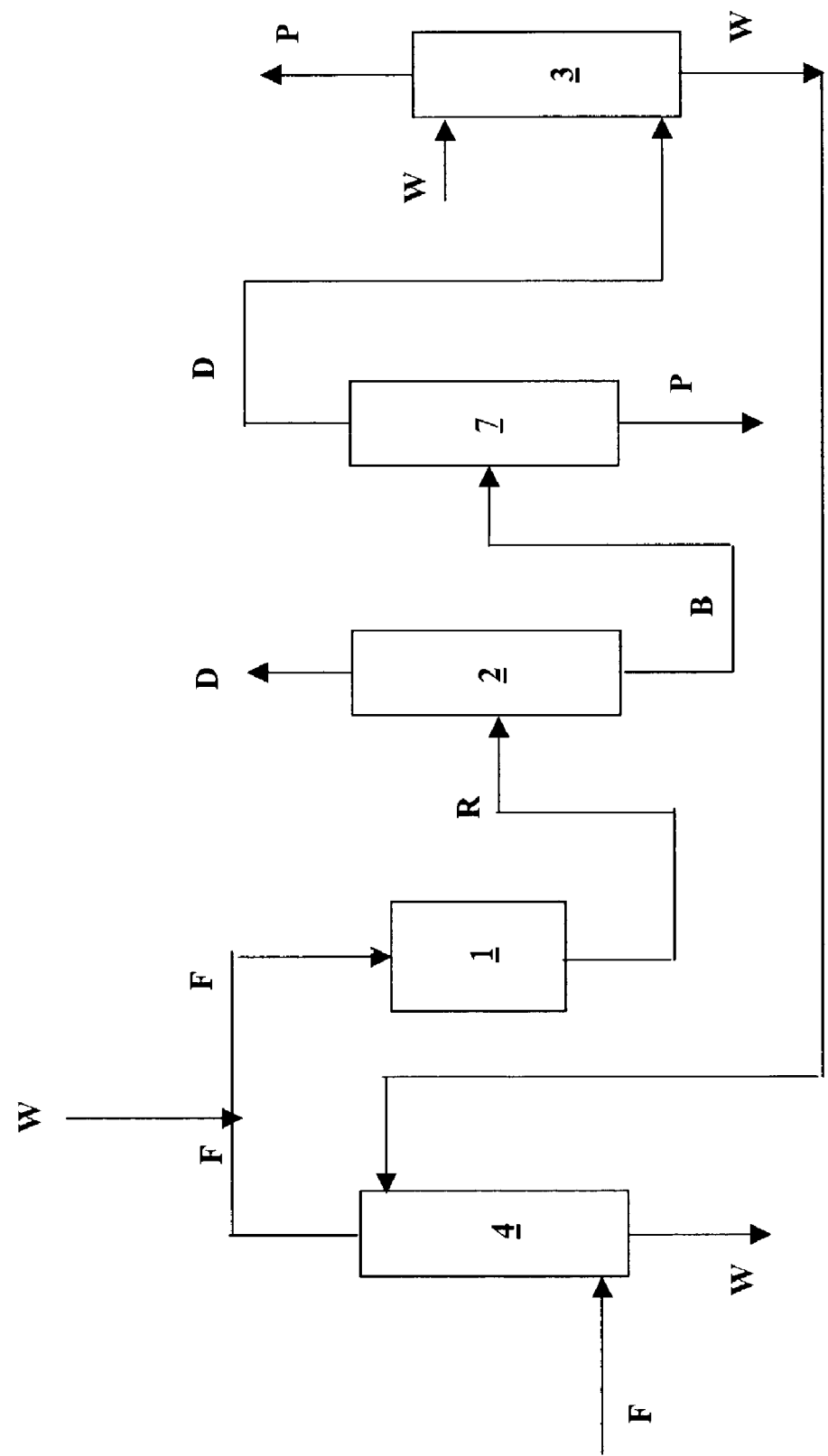
FIG. 6 is a schematic diagram of an isobutylene dimerization constructed in accordance with a fourth alternative embodiment of the present invention.

In a fourth variation of the product separation process (FIG. 6) a two-tower fractionation approach is utilized, where a first distillation column (2) and a second product distillation column (7) are placed in series. The process parameters in the distillation columns (2 and 7) are selected such that $C_3$–$C_6$ alcohol is recovered from the bottom (B1) of first distillation column (2) and further separated in the second product distillation column (7). $C_3$–$C_6$ alcohol is subsequently recovered from the top (D2) of the second product distillation column (7) and washed for recycle to the feed wash (W2).

In the preferred embodiment of the process (FIG. 3) the crude iso-octene product containing between 0.1 and 10 percent by weight of $C_3$–$C_6$ alcohol, preferably between 1 and 3 wt %, is contacted with wash water in a counter-current product extraction column containing suitable plates or packing for effective liquid-liquid contact. The product extraction column may represent between 1 and 10 theoretical extraction stages, preferably between 3 and 7, and the wash water flow to crude iso-octene flow ratio is maintained at 0.1 to 10 by weight, preferably between 2 and 4 by weight.

In the preferred embodiment more than 95%, preferably more than 99%, of the $C_3$–$C_6$ alcohol is recovered from the crude iso-octene product and dissolved in the wash water.

In the preferred embodiment of the process (FIG. 3) the wash water leaving the product extraction column containing 0.1 to 10 wt % $C_3$–$C_6$ alcohol, preferably between 0.5 and 2 wt %, is sent to the alcohol distillation column, containing suitable trays of packing for effective vapor liquid contacting as is practiced in distillation techniques. The alcohol distillation column may contain between 5 and 50 theoretical distillation stages, preferably between 15 and 25. In the preferred embodiment a concentrated alcohol stream is produced at the top of the column containing between 5 and 75 wt % $C_3$–$C_6$ alcohol, preferably between 20 and 40 wt %, whereas the bottom product from the column is essentially free of alcohol.

In the preferred embodiment of the process shown in FIG. 3, the hydrocarbon feed to the dimerization process consisting mostly of $C_4$–$C_5$ olefin and paraffin is contacted with $C_3$–$C_6$ alcohol containing wash water in a counter-current feed extraction column containing suitable plates or packing for effective liquid-liquid contact. The extraction column may represent between 1 and 10 theoretical extraction stages, preferably between 3 and 7, and the wash water flow to hydrocarbon flow ratio is maintained at 0.01 to 10 by weight, preferably between 0.1 and 1 by weight. In the preferred embodiment more than 95%, preferably more than 99%, of the $C_3$–$C_6$ alcohol is recovered from the wash water and recovered into the hydrocarbon feed.

The present product separation process is especially suitable for the conversion of existing processing units, such as MTBE plants, to the isobutylene dimerization service. In many cases existing distillation and extraction equipment can be utilized for the services in the new product separation process. This new process is especially advantaged in the fact that it results in a very high overall recovery of $C_3$–$C_6$ alcohol from the reaction effluent, at a minimum of energy consumption, contrary to other recovery methods requiring fractionation exclusively. In addition, the product separation process produces an iso-octene product containing essentially no water-soluble components which is an advantage in light of environmental impacts in handling of the gasoline product in which the iso-octene product may be blended.

While the present invention has been disclosed and described in terms of a preferred embodiment, the invention is not limited to the preferred embodiment. For example, it will be understood that the equipment in which the various fluid streams are contacted with other fluid streams be modified in number, shape, size, and configuration. In addition, various modifications to the operating conditions, feedstocks, and recycle rates, among others, can be made without departing from the scope of the invention. In the claims that follow, any recitation of steps is not intended as a requirement that the steps be performed sequentially, or that one step be completed before another step is begun, unless explicitly so stated.

EXAMPLE

One typical material balance is presented to describe the alcohol recovery with back-extraction for dimerization where isobutylene from FCC C4 stream has been dimerized. The material balance covers basically the process scheme presented in FIG. 3.

The material balance in Table 1 shows how tert-butyl alcohol and sec-butyl alcohol are recovered in extractor 3 from the bottom product (B1) of product distillation (2) and how these alcohols are extracted back into the feed in extractor 4.

TABLE 1

Material balance for back extraction of alcohols (compare FIG. 3)

| Component | P1 wt-% | W3 wt-% | B1 wt-% |
|---|---|---|---|
| $C_4$ Hydrocarbons | 1.14 | 200 ppm | |
| $C_5$–$C_7$ Hydrocarbons | Balance | 0.1 | |
| $C_8$ Hydrocarbons | 69.40 | 20 ppm | |
| $C_{9+}$ Hydrocarbons | 9.52 | | |
| $C_8$ Oxygenates | 3.21 | | |
| Tert-Butyl alcohol | 6 ppm | 14 ppm | 0.5 |
| Isopropyl and sec-butylalcohol | 0.16 | 22 ppm | 4.2 |
| Water | 0.17 | Balance | |

What is claimed is:

1. A method for improving the efficiency of a dimerization reactor that receives a hydrocarbon feed and produces a first output stream comprising a light hydrocarbon component, a dimer and an alcohol component, comprising the steps of:
   (a) separating the first output stream into a top stream containing the light hydrocarbon component and a bottom stream containing the dimer and selecting the process parameters for the separation such that the alcohol component is divided between the top stream and the bottom steam;
   (b) contacting at least one of the bottom and top streams with a water stream so as to extract at least a major portion of the alcohol component therefrom, thereby forming an water/alcohol stream;
   (c) contacting at least a portion of the water/alcohol stream with a hydrocarbon stream so as to extract at least a major portion of the alcohol present in the water/alcohol stream into the hydrocarbon stream, thereby forming an alcohol-enriched hydrocarbon stream; and
   (d) feeding the alcohol-enriched hydrocarbon stream into the dimerization reactor.

2. The method according to claim 1 wherein the hydrocarbon stream in step (c) is the hydrocarbon feed stream.

3. The method according to claim 1 wherein step (b) is carried out in a counter-current liquid-liquid extraction tower.

4. The method according to claim 1 wherein step (b) is carried out at a temperature between about 0 and 200° C.

5. The method according to claim 1 wherein the light hydrocarbon component comprises $C_{\leq 4}$.

6. The method according to claim 1 wherein step (c) is carried out in a counter-current liquid-liquid extraction tower.

7. The method according to claim 1 wherein step (c) is carried out at a temperature between about 0 and 200° C.

8. The method according to claim 1 wherein step (d) includes feeding an amount of water into the dimerization reactor along with the alcohol-enriched hydrocarbon stream.

9. The method according to claim 1 wherein step (d) includes feeding a portion of the water/alcohol stream into the dimerization reactor along with the alcohol-enriched hydrocarbon stream.

10. The method according to claim 1, further including, the step of:
   (b1) separating a portion of the water in the water/alcohol stream as a clean water stream before step (c).

11. The method according to claim 10 wherein the clean water stream formed in step (b1) forms at least a portion of the water stream in step (b).

12. The method according to claim 10 wherein step (b1) is carried out by distillation or stripping.

13. The method according to claim 10, further including the step of:
   (b2) contacting the hydrocarbon feed with at least a portion of the clean water stream formed in step (b1).

14. A method for improving the efficiency of a dimerization reactor that receives a hydrocarbon feed and produces a first output stream comprising a light hydrocarbon component, a dimer and an alcohol component, comprising the steps of:
   (a) separating the first output stream into a top stream containing the light hydrocarbon component and substantially all of the alcohol component and a bottom stream containing the dimer;
   (b) contacting the top stream with a water stream so as to extract at least a major portion of the alcohol component therefrom, thereby forming an water/alcohol stream;
   (c) contacting at least a portion of the water/alcohol stream with a hydrocarbon stream so as to extract at least a major portion of the alcohol present in the water/alcohol stream into the hydrocarbon stream, thereby forming an alcohol-enriched hydrocarbon stream; and
   (d) feeding the alcohol-enriched hydrocarbon stream into the dimerization reactor.

15. The method according to claim 14 wherein the hydrocarbon stream in step (c) is the hydrocarbon feed stream.

16. The method according to claim 14 wherein step (b) is carried out in the presence of excess water.

17. The method according to claim 14 wherein step (b) is carried out in a counter-current liquid-liquid extraction tower.

18. The method according to claim 14 wherein step (b) is carried out at a temperature between about 0 and 200° C.

19. The method according to claim 14 wherein the light hydrocarbon component comprises $C_{\leq 4}$.

20. The method according to claim 14 wherein step (c) is carried out in a counter-current liquid-liquid extraction tower.

21. The method according to claim 14 wherein step (c) is carried out at a temperature between about 0 and 200° C.

22. The method according to claim 14, further including the step of:
   (b1) separating a portion of the water in the water/alcohol stream as a clean water stream before step (c).

23. The method according to claim 22 wherein the clean water stream formed in step (b1) forms at least a portion of the water stream in step (b).

24. The method according to claim 22 wherein step (b1) is carried out by distillation or stripping.

25. The method according to claim 22, further including the step of:
   (b2) contacting the hydrocarbon feed with at least a portion of the clean water stream formed in step (b1).

26. The method according to claim 14 wherein step (d) includes feeding an amount of water into the dimerization reactor along with the alcohol-enriched hydrocarbon stream.

27. The method according to claim 14 wherein step (d) includes feeding a portion of the water/alcohol stream from step (b) into the dimerization reactor along with the alcohol-enriched hydrocarbon stream.

* * * * *